(12) United States Patent  (10) Patent No.: US 9,198,641 B2
Slowey et al.  (45) Date of Patent: *Dec. 1, 2015

(54) SPECIMEN SAMPLE COLLECTION SYSTEM

(75) Inventors: Paul Slowey, Vancouver, WA (US); Jason Giddings, Forest Grove, OR (US)

(73) Assignee: OASIS DIAGNOSTICS, CORPORATION, Vancouver, WA (US)

( * ) Notice: Subject to any disclaimer, the term of this patent is extended or adjusted under 35 U.S.C. 154(b) by 652 days.

This patent is subject to a terminal disclaimer.

(21) Appl. No.: 13/088,329

(22) Filed: Apr. 15, 2011

(65) Prior Publication Data

US 2012/0067144 A1  Mar. 22, 2012

Related U.S. Application Data

(63) Continuation-in-part of application No. 12/419,939, filed on Apr. 7, 2009, now Pat. No. 8,025,851.

(60) Provisional application No. 61/324,321, filed on Apr. 15, 2010.

(51) Int. Cl.
*A61B 10/00* (2006.01)

(52) U.S. Cl.
CPC ..... *A61B 10/0051* (2013.01); *A61B 2010/0006* (2013.01); *A61B 2562/0295* (2013.01)

(58) Field of Classification Search
CPC .................. A61B 10/0051; A61B 2010/0006; A61B 2562/0295

See application file for complete search history.

(56) References Cited

U.S. PATENT DOCUMENTS 4,353,868 A   10/1982  Joslin et al.
4,895,808 A    1/1990  Romer (Continued)

*Primary Examiner* — Sam P Siefke

(74) *Attorney, Agent, or Firm* — Mark E. Beatty; Kurt M. Rylander; Rylander & Assoc. PC

(57) ABSTRACT

A specimen sample collection system includes a handle having opposing first and second ends, and a sufficiency indicator coupled to the handle, wherein the handle second end and sufficiency indicator form a cavity adapted to receive a sample collection pad; a sample collection pad having opposing ends, the sample collection pad partially contained within and extending from the handle second end and in contact with the sufficiency indicator, the sample collection pad having a cylindrical cross section; and, a pad compression tube having a first open end to go over the sample collection pad and second end of the handle, an opposing second end, an interior surface extending therebetween, and at least outlet port proximal to the pad compression tube second end and in fluid communication with the pad compression tube interior. The system may include wherein the sufficiency indicator is a light pipe or other indicating element, providing visual, aural or haptic indication of sufficient sample volume. The system may include wherein the sufficiency indicator includes longitudinal channels extending along the interior surface in contact with the sample collection pad to provide a path for displace air. The system may include a sealing member to seal against a pad compression tube and to engage the specimen collection pad. The system may include one or more collection tubes attachable to one or more of the pad compression tube outlet ports. The system may include ergonomic features for the handle and pad compression tube. The system may include a specimen collection pad having a full cross section portion and a reduced cross section portion, including a shoulder to engage a sealing member and an angled surface to conform to the interior surface of a light pipe sufficiency indicator. The system may include one or more in-line filters adjacent the pad compression tube outlet ports. The system may include additional features as described herein.

38 Claims, 15 Drawing Sheets

(56) References Cited

U.S. PATENT DOCUMENTS

| | | |
|---|---|---|
| 4,931,051 A | 6/1990 | Castello |
| 5,016,982 A | 5/1991 | Fergason et al. |
| 5,393,496 A | 2/1995 | Seymour |
| 5,494,646 A | 2/1996 | Seymour |
| D369,664 S | 5/1996 | Dye |
| 5,922,614 A | 7/1999 | Cesarczyk |
| 5,962,336 A | 10/1999 | Sun |
| 6,046,058 A | 4/2000 | Sun |
| 6,187,598 B1 | 2/2001 | May et al. |
| 6,258,548 B1 | 7/2001 | Buck |
| 6,365,417 B1 | 4/2002 | Fleming et al. |
| 6,372,516 B1 | 4/2002 | Sun |
| 6,416,715 B1 | 7/2002 | Gambert et al. |
| 6,423,550 B1 | 7/2002 | Jenkins et al. |
| 7,618,591 B2 * | 11/2009 | Slowey et al. .............. 422/412 |
| 7,927,548 B2 * | 4/2011 | Slowey et al. .............. 422/422 |
| 8,025,851 B2 * | 9/2011 | Slowey et al. .............. 422/420 |
| 8,273,305 B2 * | 9/2012 | Slowey et al. .............. 422/405 |
| 2003/0064526 A1 | 4/2003 | Niedbala et al. |
| 2003/0205097 A1 | 11/2003 | Wickstead et al. |
| 2004/0014203 A1 | 1/2004 | Wickstead et al. |
| 2009/0306543 A1 | 12/2009 | Slowey et al. |

* cited by examiner

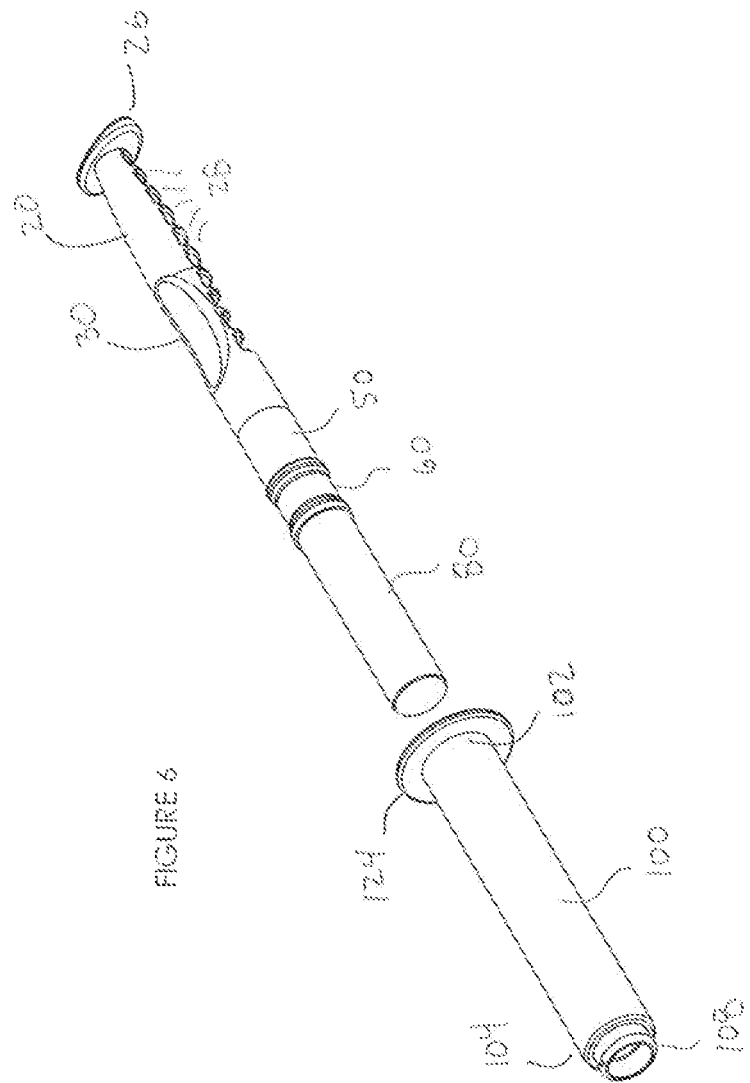

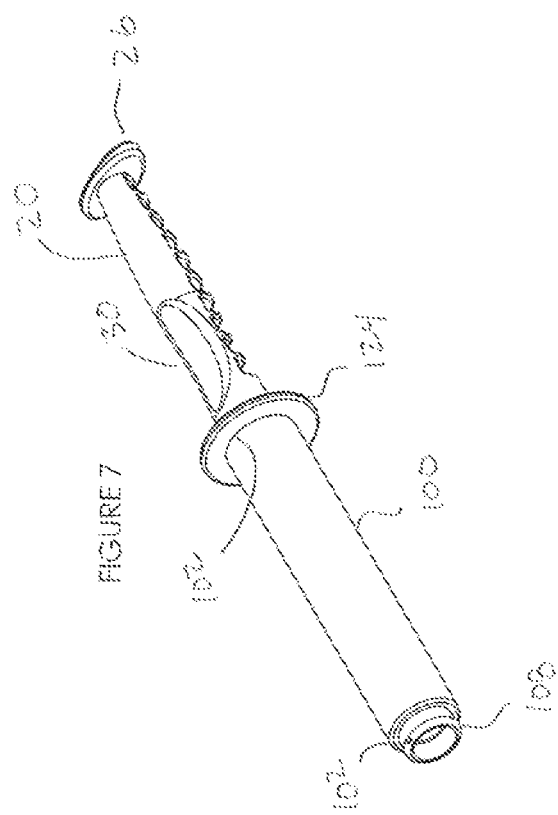

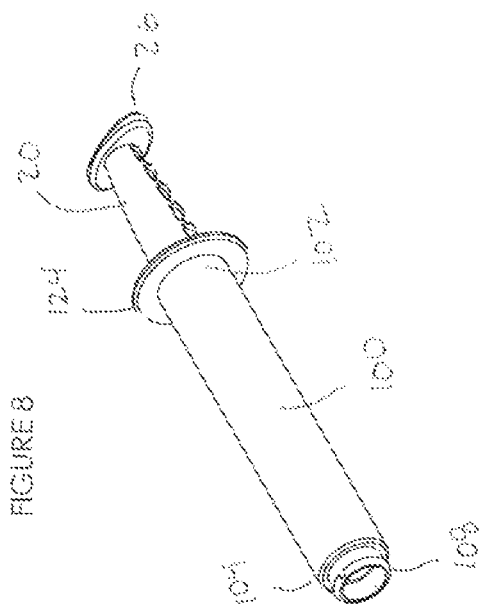

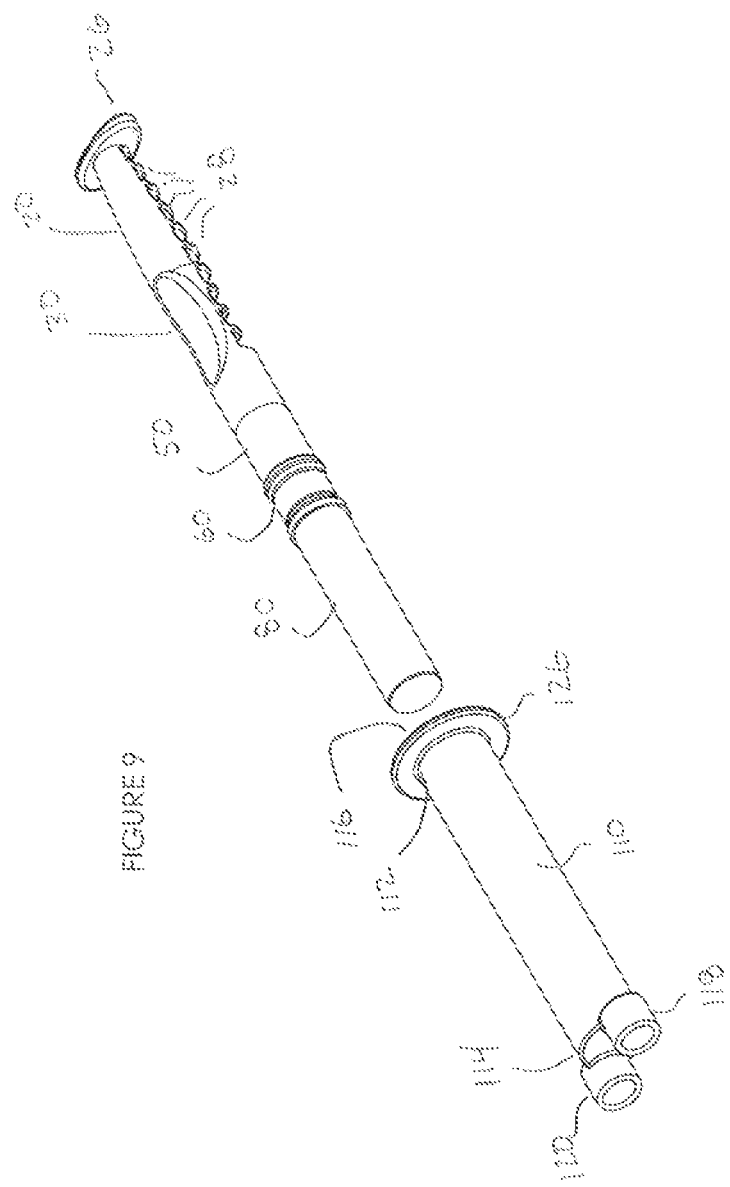

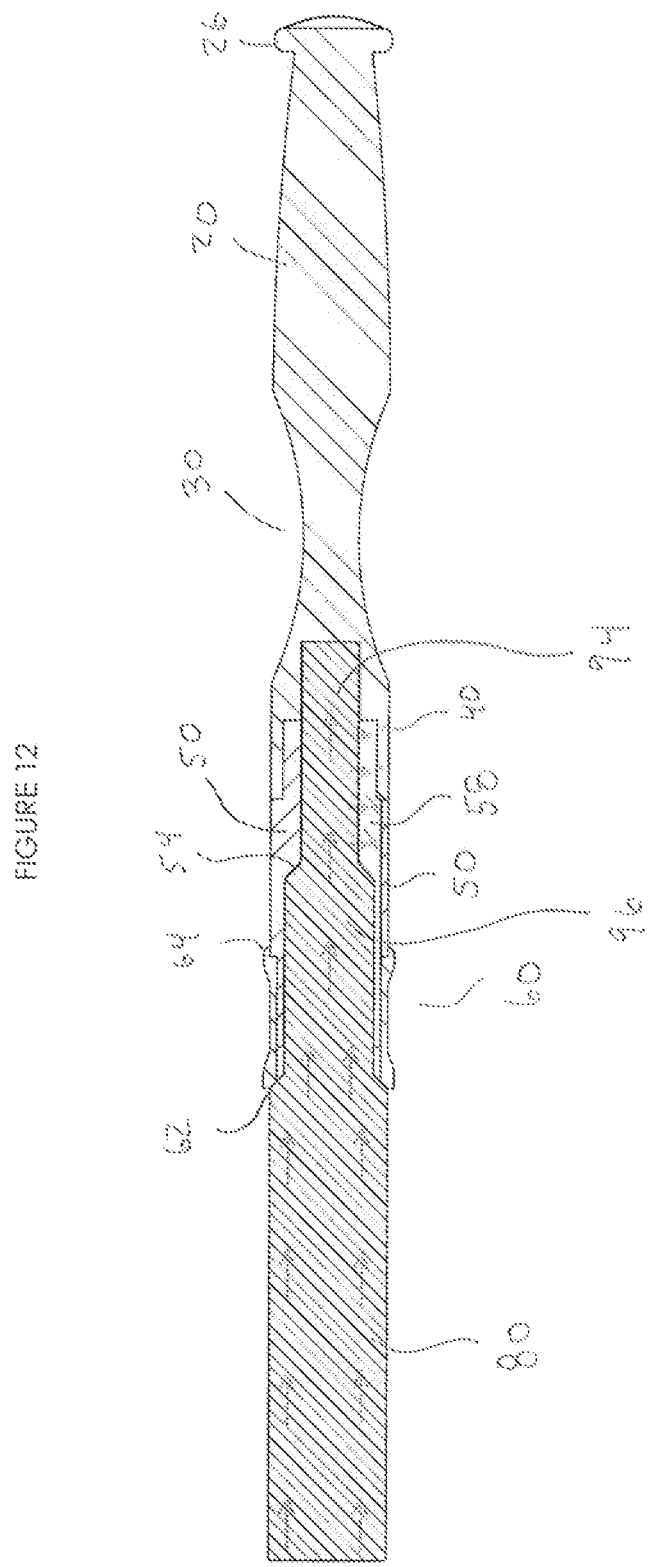

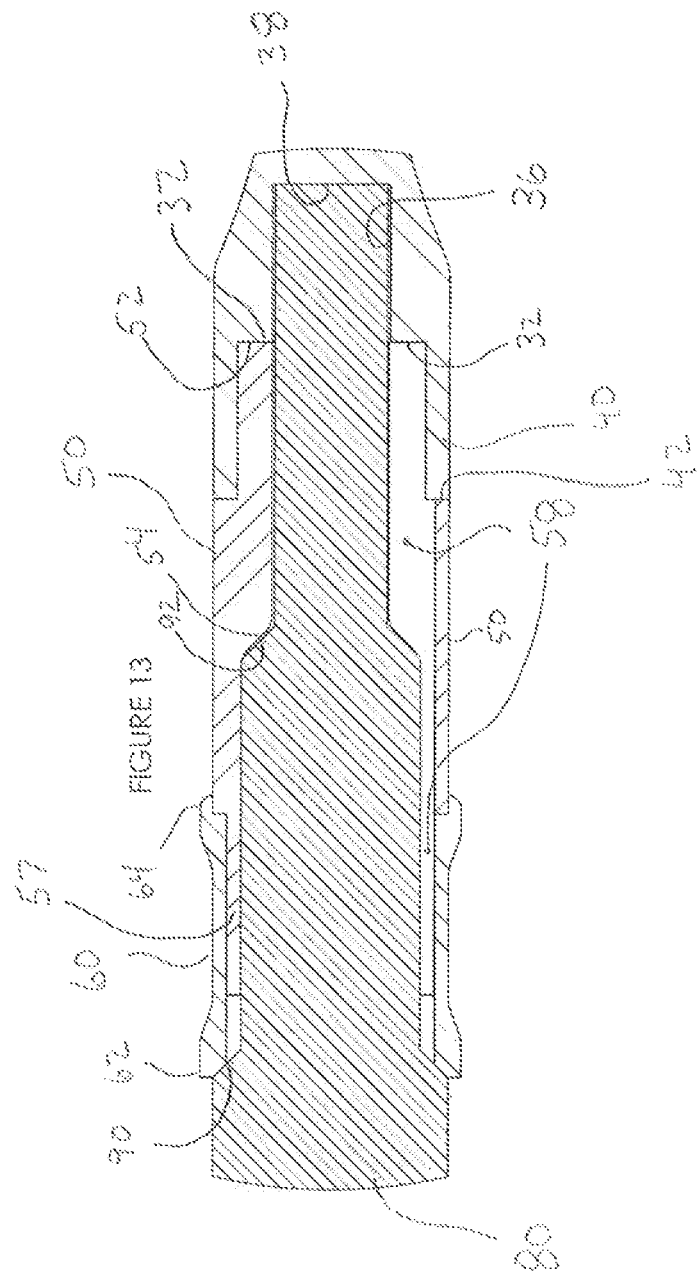

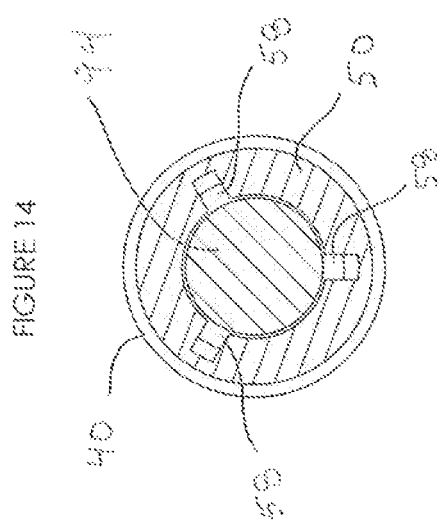

SPECIMEN SAMPLE COLLECTION SYSTEM

CROSS-REFERENCE TO RELATED APPLICATIONS

This application is claims priority to U.S. Provisional Application Ser. No. 61/324,321 filed Apr. 15, 2010, and to co-pending U.S. Nonprovisional application Ser. No. 12/419,939 filed Apr. 7, 2009, the disclosures of each of which are hereby incorporated by reference into this application.

FIELD OF THE INVENTION

The present invention relates to devices for collecting fluid samples by absorbing the fluid into an absorbent material and then expelling the collected fluid into a sample container.

BACKGROUND

Over the last few years there has been a tremendous growth in the area of salivary diagnostics, prompted in part by efforts from the National Institutes of Health (NIH) and its National Institute of Dental and Craniofacial Research (NIDCR) division to promote the development of non-invasive technologies for the diagnosis of diseases and measurement of specific analytes or molecules in saliva or oral fluid samples. These agencies have made funding available for the development of novel, innovative tools including microarrays, lab-on-a-chip, lateral flow, ELISA and other technologies using saliva and other non-invasive sampling methodologies. Other reasons for the increased interest in salivary diagnostics include the development of important new technologies for both the collection and testing of oral fluids and improvements in the manufacturability of such devices.

There are several successful corporate stories in salivary diagnostics that are also prompting other companies to search out opportunities in non-invasive testing. For instance, it is now possible to detect HIV antibodies from oral specimens at the point-of-care using the OraQuick® HIV 1/2 rapid antibody test (OraSure Technologies, Bethlehem Pa., USA) with greater than 99% sensitivity and specificity. This company is currently proceeding with an FDA submission that would allow consumers to purchase such a test over the counter in a pharmacy.

In the United States millions of oral specimens are collected and processed in the Public Health and insurance market sectors for HIV antibodies, cotinine (nicotine) for smoking and cocaine as part of a "risk assessment" profile. Additionally, options for testing Federal employees for a range of abused drugs using non-invasive methods including saliva are readily accepted by SAMHSA, the Substance Abuse Mental Health Services Administration (the US Government body responsible for drug testing in the Federal workplace). Such testing is also common in the workplace environment where corporations in the US (and other parts of the world) use saliva as part of pre-employment and random drug testing policies.

General wellness is monitored by testing various steroid hormones in the laboratory. Home collection using a standardized saliva collection kit is common place and a large number of testing laboratories have appeared offering a multitude of test options for the "worried well". Tests include a range of male and female hormones including testosterone, estradiol, progesterone, cortisol and others. In these situations no "diagnosis" is provided on collected samples. Instead, a Medical Director from the laboratory will provide an indication of the levels of a specific target analyte in the saliva and make recommendations on suitable lifestyle changes or perhaps an imminent visit to the doctor.

The future for saliva testing also holds great promise since the publication of the entire salivary proteome by the Human Saliva Proteome Consortium, a group headed by Dr. David Wong from UCLA. The widespread publication of the identity of 1,166 proteins potentially implicated in disease progression will lead to the rapid growth in new applications for salivary diagnosis. Already in development are a diagnostic device for the rapid detection of the drug phenytoin, which uses a surface plasma resonance imaging instrument, an oral fluid Nanosensor test that measures four oral fluid markers as an indication of oral cancer and a lab-on-a-chip technology for point-of-care detection of salivary biomarkers in periodontitis, among a number of others. An excellent review of these and other new applications for oral fluid diagnostics was published following a landmark meeting of many researchers in the field at Lanier Lakes, Ga. USA in October 2006. The monograph published following the meeting is available from the New York Academy of Sciences.

Tools for oral fluid diagnosis may be categorized as one of two types. The first is diagnostic devices providing an immediate diagnosis or test result, so-called "point-of-care" or "near-patient" tests. This category includes the manual OraQuick® rapid HIV 1/2 antibody test that employs lateral flow immunochromatographic technology and the prototype Oral Fluid Nanosensor (OFNASET) Test device from Dr. David Wong's UCLA laboratory, which relies on microfluidics, nanotechnology in a hand-held reading device to potentially screen for oral cancer. This technology detects a series of four salivary molecular RNA markers. Another example among many others is a rapid point-of-care drug screening technology called RapiScan® from Cozart Biosciences (Abingdon, UK), which is used to screen would be drug offenders at the roadside using saliva samples. Many other rapid diagnostic products exist which require saliva sampling or testing, but such products are outside the scope of this application.

The other side of the market for salivary diagnostics involves the collection of oral fluids and the subsequent transportation of the samples to a laboratory, or other remote site where the testing is performed. Again many examples exist. Examples include the collection of oral samples for HIV testing for Public Health and also for insurance risk assessment, where oral specimens are collected using the OraSure® Oral Fluid Collection Device (OraSure Technologies, Bethlehem Pa., USA) and sent to a laboratory. Typically, specimens are analyzed using traditional ELISA technology for the detection of HIV, cotinine (nicotine), cocaine and others. Others include collection of saliva specimens for drug testing in the workplace environment for pre-employment purposes or random drug testing. In such situations saliva is collected using one of a number of available commercial saliva collection devices (including Intercept™ from OraSure Technologies, Bethlehem Pa., USA, Quanti-SAL™ from Immunalysis Corporation, Pomona Calif., USA, Aware Messenger™ from Calypte Biomedical, Lake Oswego, Oreg. USA and Salivette®, Sarstedt, Germany among others) then sent to a laboratory where a battery of drug tests including marijuana (THC), cocaine, opiates (heroin), methamphetamine, amphetamine, and phencyclidine is tested on the processed saliva. Similar practices are observed in Federal workplace and military drug testing environments.

A small industry has emerged for salivary hormone testing where laboratories provide saliva collection kits and a test menu for home users. Clients expectorate into a tube that is subsequently sent to a laboratory. As part of the service subjects are able to request testing for various steroid hormones as part of a general wellness screening panel. The results provide an indication of general health and wellness, without providing any definitive diagnosis.

Very recently a new industry has emerged for "personal genome" testing in what is termed the "consumer genetics" market. In this area saliva or buccal cell swab samples are collected in the home and sent to a laboratory and tested for specific genetic markers and single nucleotide polymorphisms (SNPs) that provide information on the parentage of the individual in question, predisposition to specific diseases, ancestry and other genetic information. The number of companies in this area is rapidly growing but at this time, the recognized market leading companies are 23andMe, Navigenics, DeCode Genetics, Knome, Illumine, and Sciona. The convenience and non-invasiveness makes saliva very attractive for home testing/home collection products. Other applications in this market sector will be addressed in further detail below.

In general, multi-purpose saliva collection is facilitated using one of a number of commercially available saliva collection devices or by expectoration ("spitting") into a sample receptacle. A number of devices are now available to collect specimens and these include the OraSure® device (OraSure® Technologies), Aware Messenger™, Salivette, Omni•SAL® (Stat-Sure Diagnostics, Framingham, Mass., USA), ORACOL (Malvern Medical Developments, UK), Cozart Oral Swab (Cozart BioSciences, Abingdon, UK) and the Versi•SAL® device (Oasis Diagnostics® Corporation, Vancouver, Wash. USA). With the exception of the Versi•SAL® device, which provides the opportunity to use multiple absorbent materials, customized to specific applications, these products have limited applications. This is mainly due to limitations in the number and type of absorbent materials used to perform the saliva collection operation. While each of the above methodologies may be considered appropriate for certain applications in salivary testing, none of these devices is appropriate for the collection, stabilization, transportation and extraction of purified DNA from saliva. This in turn has restricted the use of salivary DNA for "downstream" applications particularly the potential use of saliva specimens for molecular diagnostic testing.

Molecular diagnostics is one of the fastest growing areas in the area of clinical and animal diagnostics. The current market for molecular diagnostics is estimated to be $3.2 billion (2007 figures) and forecast to reach $5.4 billion by 2012. In this area of clinical diagnostics traditional blood testing is by far the current method of choice. In current protocols, specimens are collected in a blood tube, usually by a trained phlebotomist, and sent to the laboratory. Upon receipt at the laboratory, the sample is initially separated from unwanted blood by-products then further purified prior to analysis. Blood samples contain potentially infectious agents and the cost of transportation can be expensive. In addition, all samples must be treated as infectious waste and disposed of according to recognized safety standards, which can also be costly. If a device was available to collect salivary DNA for clinical diagnostic testing this would offer several advantages over current blood testing algorithms and would be welcomed in clinical practice as a step forward. From the patient's perspective it would eliminate painful blood draws associated with current testing. In addition it would eliminate the need for a trained phlebotomist to draw the blood sample, as well as alleviate any potential for infection from tainted blood samples. Overall, saliva sampling is generally cheaper and does not require an additional pre-treatment step (as required for blood), to separate the required salivary component prior to analysis.

As described previously, there are a number of commercially available saliva collection devices on the market. In most cases, these devices incorporate some sort of absorbent material that is used to collect the saliva specimen. The sample is subsequently removed from the absorbent material using methods such as squeezing, centrifugation or simply soaking in a buffer to solubilize the target analytes. These devices work well for the collection of certain molecules such as infectious disease antibodies (including HIV, hepatitis B, hepatitis C and others), hormones, cancer biomarkers and drugs, for instance, but none of these may be applied to the collection and retrieval of DNA (Deoxy Ribonucleic Acid) or RNA (Ribo Nucleic Acid), which requires a device with very specific performance characteristics. This is due to an inherent property of current devices to bind DNA and RNA moieties to the fibers of the absorbent material used to collect the specimen. DNA binds tightly to the fibers and is not easily removed. Any effort to remove the DNA, cells using reagents, organic solvents usually results in denaturation of the DNA molecules and subsequently observed recoveries are poor.

Some of the above limitations have been overcome in a few devices that do successfully facilitate salivary DNA collection. Expectoration (spitting in a cup or other vessel) provides a saliva sample that can be successfully stabilized and purified through available methodologies to yield high quality DNA, and this method is in use in various testing strategies, however this method lacks adequate standardization (sample variability) and is not considered elegant or dignified.

Over the last few years other promising devices have emerged that are based upon modifications to the traditional expectoration technique. The most widely used of these is the OraGene® DNA device from DNA Genotek (Ottawa, Ontario, Canada). OraGene® is a more sophisticated way to collect saliva into a vessel to which is attached a screw-on cap. In the screw-on cap is a mixture of preservative buffers. Upon completion of the expectoration process, the cap is screwed onto the device releasing the preservative buffer, which drops into the saliva, is mixed by shaking and then acts to protect the integrity of the sample until processing and extraction can take place. The same company has recently perfected the OraGene® RNA device for the collection of RNA from oral fluid specimens. OraGene® RNA applies the same basic principles as used in the OraGene® DNA device. Invitek Gesellschaft für Biotechnik and Biodesign mbH (Invitek, Berlin, Germany) has come up with a similar tool, SaliGene® as an alternative "spit-in-a-cup" technology, which has additional application as a collector for stool or swab specimens (when coupled with specific extraction kits for these alternate specimen types). In the SaliGene® device, subjects expectorate into a modified collection tube until a predetermined volume has been reached. A screw-cap with attached sealing member is screwed in place and the sealing member depressed causing a preservative/lysis buffer to flow into the collected saliva specimen. The sample of mixed preservatives and saliva is gently shaken then sent to a laboratory for further processing.

Researchers from Roswell Park describe the extraction of genomic DNA from saliva using the Qiagen (Hilden, Germany) QIAamp Kit on the Qiagen website. This work was reprinted from earlier work carried out in 1997. The QIAamp kit is one of a number of kits commercially available for DNA extraction from bodily fluids. In this case as in many others, expectoration was used to collect the saliva specimens.

In collecting specimens for diagnostic testing several criteria are important. Specimens need to be collected rapidly to eliminate any opportunity for sample degradation, and they must be removed rapidly from the point of collection and stabilized promptly for subsequent transportation purposes (if necessary). The specimen device used to collect saliva should be able to withstand temperature fluctuations and the rigors of shipping products by air or road allowing samples to arrive safely at the final destination laboratory, hospital or other remote facility. The sample so obtained should be stable for extended periods of time at ambient temperatures and also at −20 degrees Celsius for long-term storage.

Devices for DNA or RNA sample collection should be robust, transportable, capable of transporting a saliva sample (or other biological fluid) containing the DNA or RNA molecules to a laboratory or other remote facility and also to provide ready sample removal for subsequent extraction using a number of commercially available, off the shelf kits. The yield of DNA/RNA produced depends upon the particular application but should be sufficient for immediate application in testing kits provided by a multitude of manufacturers for infectious diseases, oncology, cardiovascular diseases, immunological disorders and many others. Literature reports suggest that a minimum of 10 µg of pure DNA should be collected and typically even larger quantities are required. For example, 100 µg or more of pure DNA would be a preferable sample quantity.

While the limited number of examples of salivary DNA devices described above provides methods for DNA/RNA collection and extraction, none of the above devices meet the market need for a simple, elegant, standardized and rapid method for the collection of biological fluids and other biological materials, with the specific purpose of extraction of DNA and RNA, for large scale implementation.

SUMMARY AND ADVANTAGES

A specimen sample collection system includes a handle having opposing first and second ends, and a sufficiency indicator coupled to the handle, wherein the handle second end and sufficiency indicator form a cavity adapted to receive a sample collection pad; a sample collection pad having opposing ends, the sample collection pad partially contained within and extending from the handle second end and in contact with the sufficiency indicator, the sample collection pad having a cylindrical cross section; and, a pad compression tube having a first open end to go over the sample collection pad and second end of the handle, an opposing second end, an interior surface extending therebetween, and at least outlet port proximal to the pad compression tube second end and in fluid communication with the pad compression tube interior. The system may include wherein the sufficiency indicator is a light pipe or other indicating element, providing visual, aural or haptic indication of sufficient sample volume. The system may include wherein the sufficiency indicator includes longitudinal channels extending along the interior surface in contact with the sample collection pad to provide a path for displace air. The system may include a sealing member to seal against a pad compression tube and to engage the specimen collection pad. The system may include one or more collection tubes attachable to one or more of the pad compression tube outlet ports. The system may include ergonomic features for the handle and pad compression tube. The system may include a specimen collection pad having a full cross section portion and a reduced cross section portion, including a shoulder to engage a sealing member and an angled surface to conform to the interior surface of a light pipe sufficiency indicator. The system may include one or more in-line filters adjacent the pad compression tube outlet ports. The system may include additional features as described herein.

The specimen sample collection system of the present invention presents numerous advantages, including: (1) facilitation of the collection of a fluid biological sample in sufficient quantity to conduct genetic testing and any other testing requiring DNA or RNA as the sample, e.g. microarrays, PCR, genotyping, and forensic sampling; (2) inexpensive construction; (4) rapid sample collection time; (5) simple and more elegant collection method than traditional "spit-in-a-cup" technologies; (6) more amenable for large population studies and DNA collection by the patient/subject in the home; (7) rapid collection time reduces the possibility for introduction of any "foreign" DNA; (8) incorporation of a preservative/lysis buffer capable of protecting the integrity of the sample for long periods of time; (9) compatible with diverse environmental and biological fluids and fluid sample volumes; (10) visual indication that an adequate fluid sample volume has been collected; (11) incorporation of rapid testing features for certain fluid sample tests; (12) ability to divide collected fluid samples between or among several testing procedures; and (13) incorporation of a sample filter to filter out unwanted particulates or particulate contaminants.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

FIG. 6 shows a perspective view of the first embodiment.

FIG. 7 shows a perspective view of a first embodiment with a pad compression tube inserted over a sample collection pad.

FIG. 8 shows a perspective view of a first embodiment with a pad compression tube inserted over a sample collection pad and compressed.

FIG. 9 shows a first embodiment with a pad compression tube having a plurality of outlet ports.

FIG. 12 shows a cutaway side view of a first embodiment.

FIG. 13 shows a close up cutaway side view of a wrap-around light pipe of a first embodiment.

FIG. 14 a cutaway end view of a first embodiment through the wrap-around light pipe.

REFERENCE NUMBERS USED IN DRAWINGS

Figure 1:
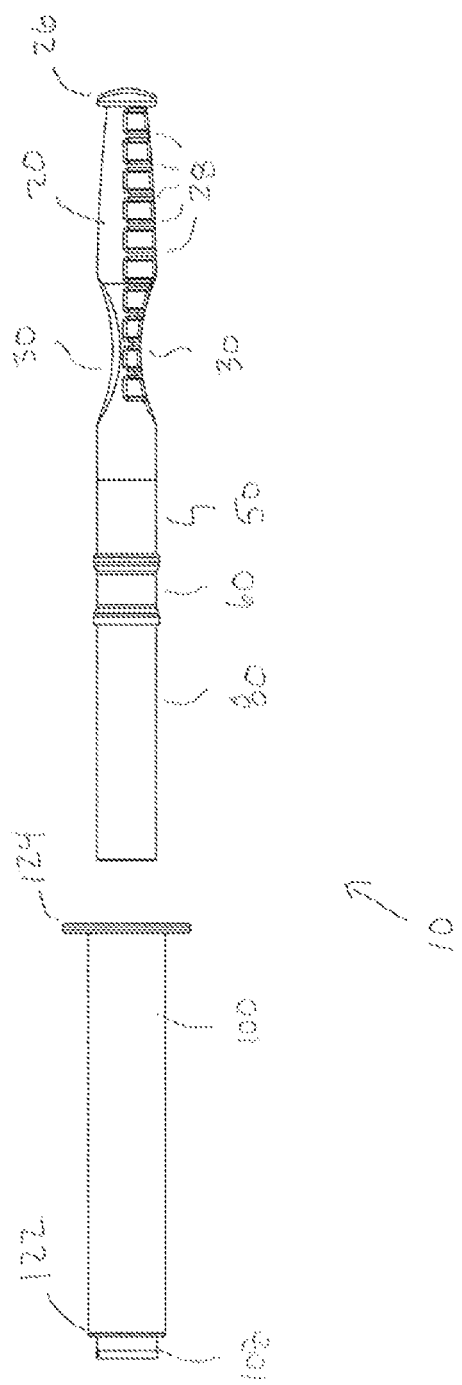
FIG. 1 shows a side view of a first embodiment.
Figure 2:
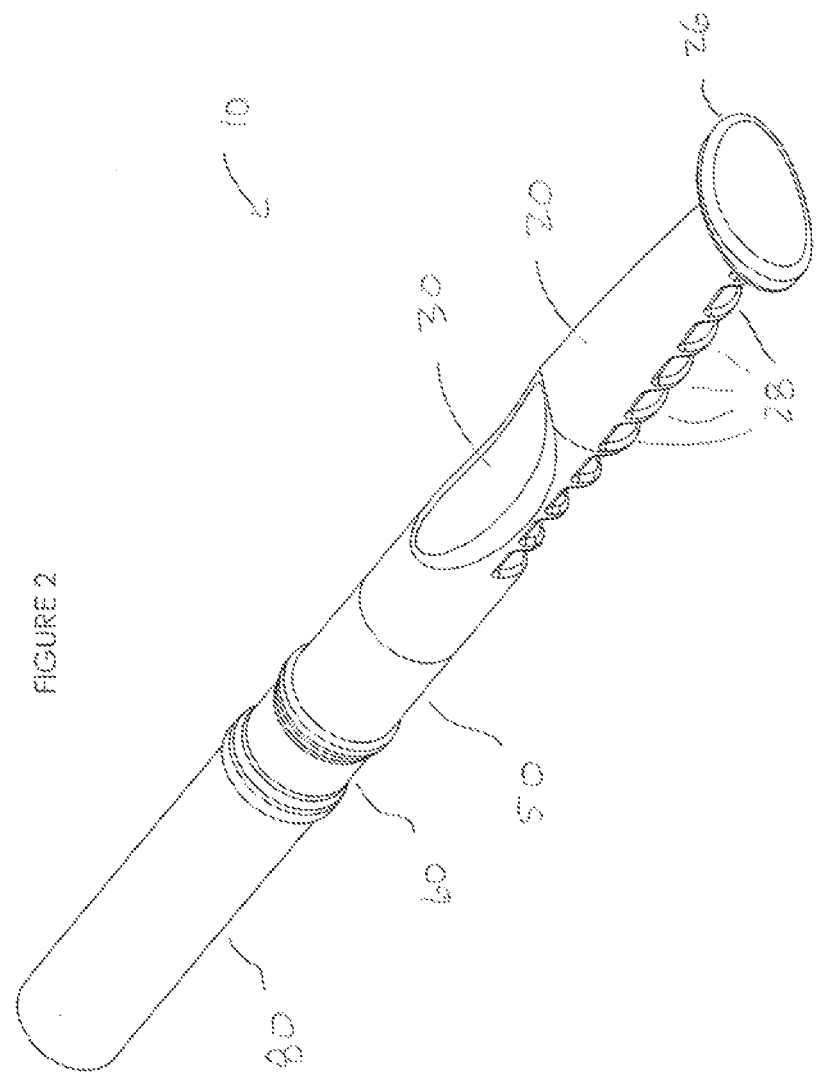
FIG. 2 a perspective view of a first embodiment.
Figure 3:
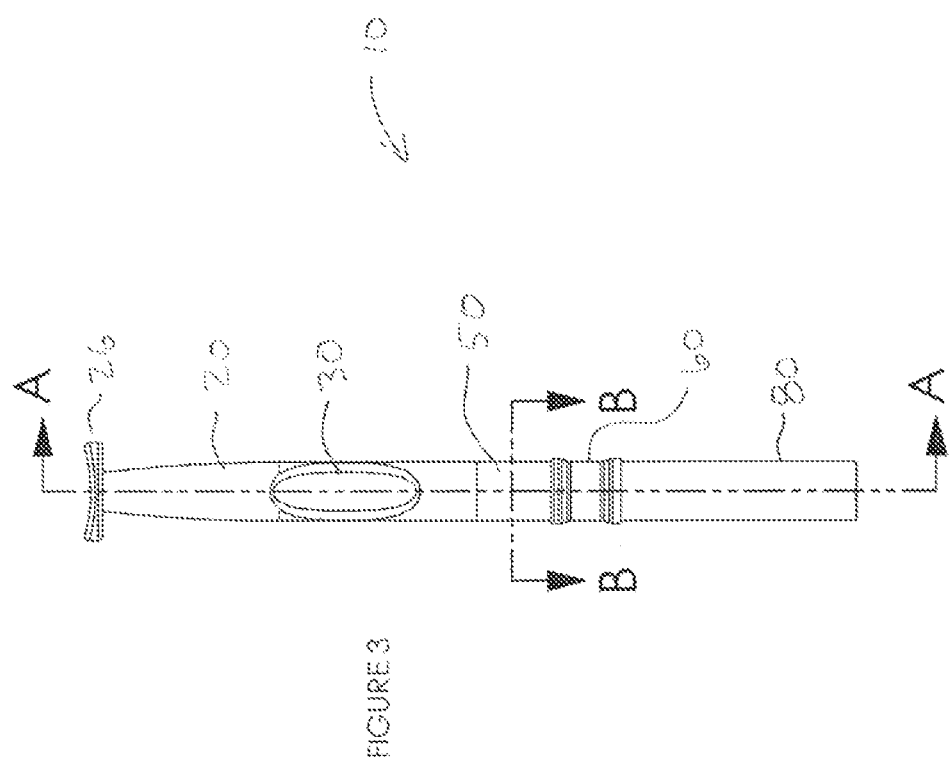
FIG. 3 shows another side view of a first embodiment.
Figure 4:
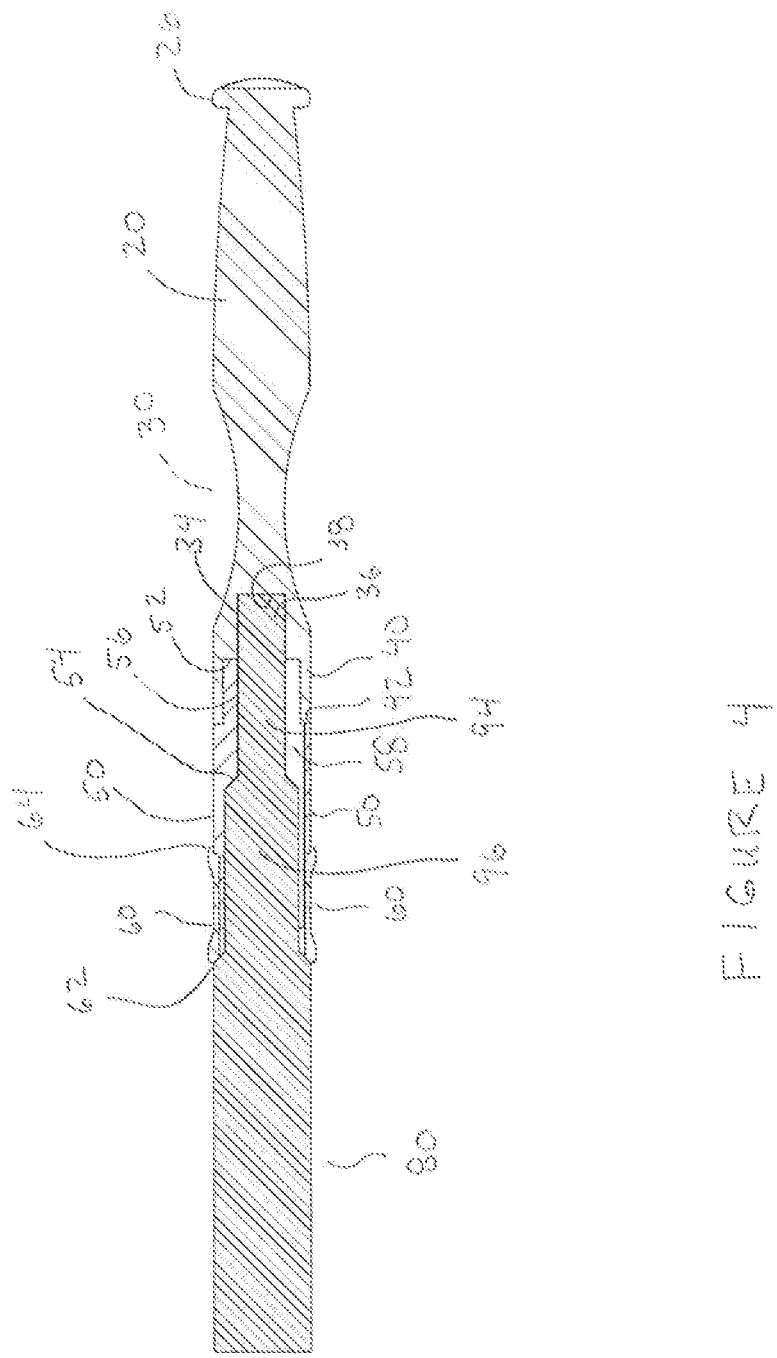
FIG. 4 shows cutaway side view of a first embodiment.
Figure 5:
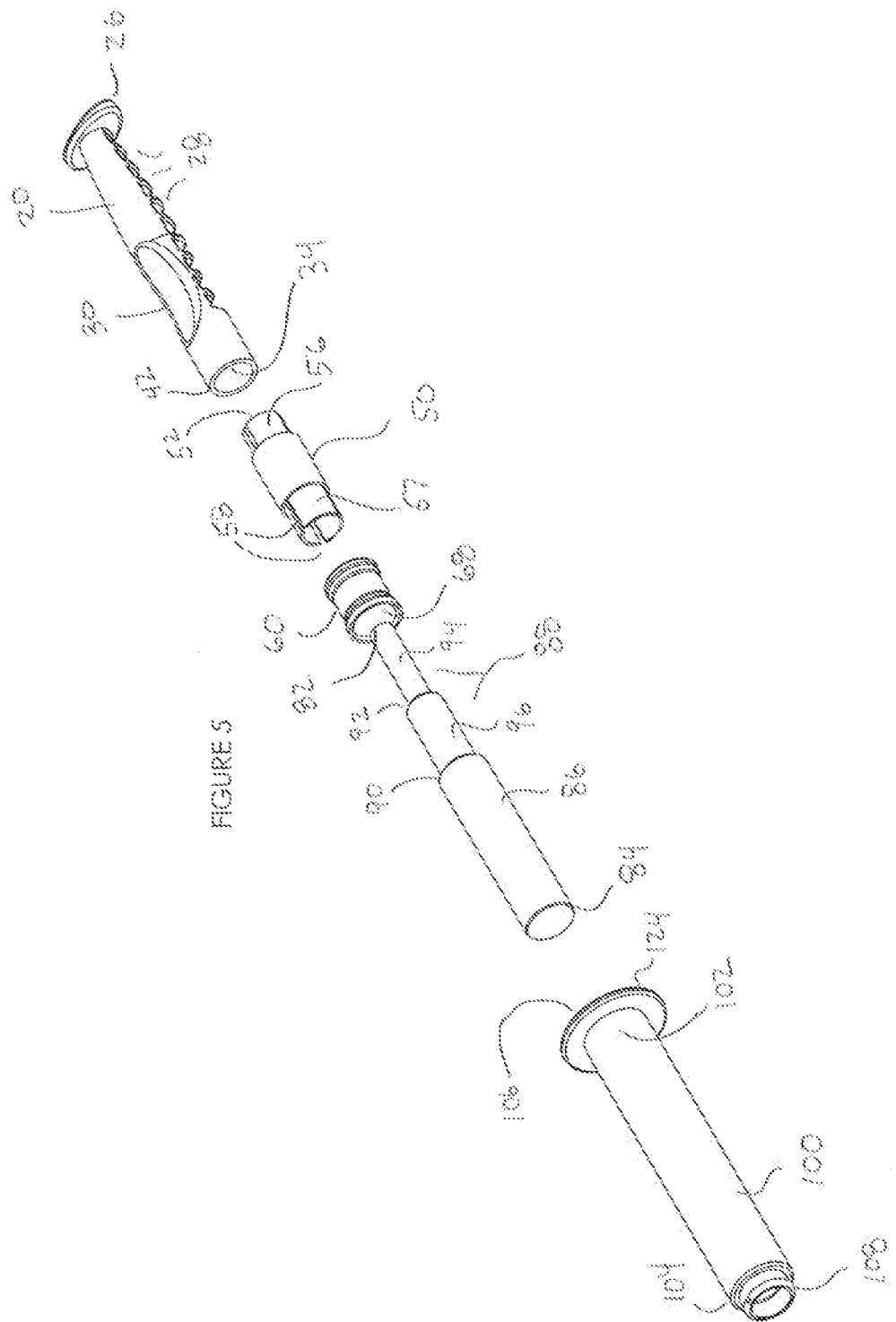
FIG. 5 shows an exploded view of a first embodiment.
Figure 11:
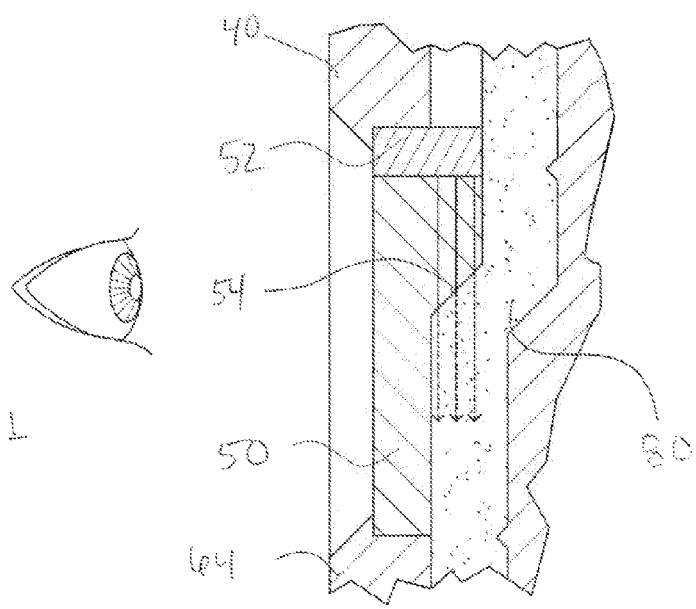
FIG. 11 shows a cutaway view of a light pipe of a first embodiment in a saturated condition
Figure 10:
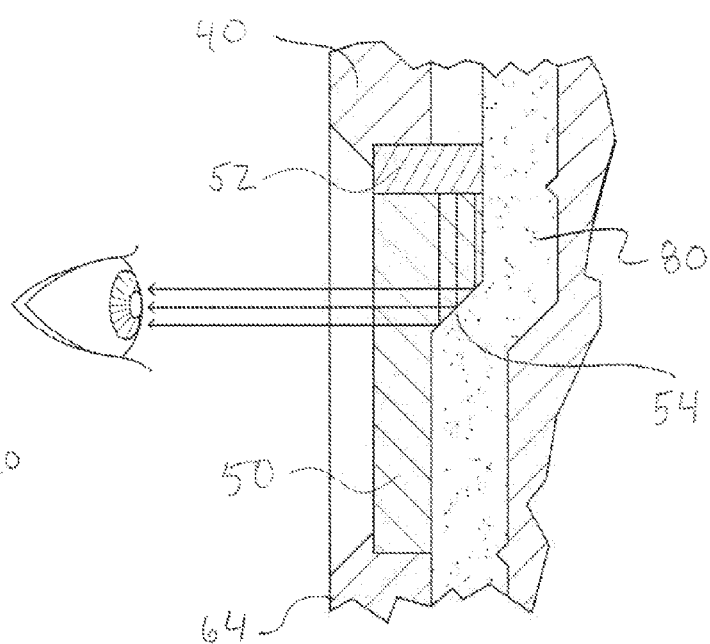
FIG. 10 shows a cutaway view of a light pipe of a first embodiment in an unsaturated condition.

Turning now descriptively to the drawings, in which similar reference characters denote similar elements throughout the several views, the figures illustrate the specimen sample collection system of an embodiment of the present invention. With regard to the reference numerals used, the following numbering is used throughout the various drawing figures:

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Referring to FIGS. 1-9, a first embodiments of a specimen sample collection system 10 is shown. More specifically, an embodiment is a specimen sample collection system 10 to facilitate collection of fluid specimens and particularly to facilitate collection of saliva specimens from human or animal species for the purpose of extracting purified DNA and/or RNA, or to test for the presence of selected proteins, antibodies or other biochemical markers. For example, DNA and/or RNA samples collected with the specimen sample collection system 10 of an embodiment may be purified by one of a number of established sample purification kits yielding samples sufficiently pure and of high quality to be used in immediate testing protocols for any test requiring DNA or RNA samples. The purified DNA and/or RNA may thereafter have downstream application in testing methods including molecular diagnostics (e.g., polymerase chain reaction, genotyping, personal genomic testing, microarrays, and lab-on-a-chip technologies). Additional types of biological and/or environmental fluid samples may be collected by the specimen sample collection system 10 of an embodiment as will be explained in more detail below.

Referring again to FIGS. 1-9, a specimen sample collection system 10 includes a handle 20 having opposing first and second ends 22 and 24, and a sufficiency indicator 50 coupled to the handle 10, wherein the handle second end 24 and sufficiency indicator 50 form a cavity 34 adapted to receive a sample collection pad 80.

Sample collection pad 80 has opposing ends 82 and 84, and is partially contained within and extending from the handle second end 24, and in contact with the sufficiency indicator 50. Sample collection pad 80 has a cylindrical cross section. In the embodiment the cross section of pad 80 is circular. In this regard, a cylindrical cross section indicates that the pad has substantial thickness in relation to its width, such as a rectangular shape or a round shape (including circular or oval shape), rather than being thin and flat. A rectangular shaped pad may have rounded corners for user comfort and to prevent excessive wear on pad edge surfaces.

Pad compression tube 100 has a first open end 102 to go over the sample collection pad 80 and handle second end 24, an opposing second end 104, an interior surface 106 extending therebetween, and at least outlet port 108 proximal to the pad compression tube second end 104 and in fluid communication with the pad compression tube interior.

In the embodiment, handle 20 includes ribbed grip members 28 disposed along a portion of its length toward handle first end 22, and a thumb pad 26. A detent 30 is also provided to enhance grip. Ribbed grip members 28 serve to enhance gripping action even with wet or sweaty hands, and reduce the amount of plastic used to form handle 20 while not weakening the structure excessively.

In the embodiment, sufficiency indicator 50 is a light pipe, but could also include one or more visual, audio, tactile, or haptic indications, or a combination thereof to indicate an adequacy of the fluid sample volume. For example, an embodiment may have a spring loaded against a dry absorbent sponge piece which is in fluid communication with a sample collection pad 80. When pad 80 becomes saturated to the location of the sponge piece, the sponge softens and releases the retained spring lever, which provides an audible snapping noise, and sensible vibration, and can be visually verified through the viewing window. Sufficiency indicator 50 may include a window coupled to a side of handle 20. In the first embodiment, sufficiency indicator 50 includes an annular portion coupled to the handle second end 24, effectively forming an extension of the handle 50.

In the embodiment, the sufficiency indicator 50 is an annular light pipe including a first end surface 52 and a second surface 54 in physical contact with the sample collection pad 80 creating a refractive boundary, the second surface 54 oriented at an angle of incidence to the first end surface 52 such that when the sample collection pad 80 absorbs a sufficient liquid sample the refractive properties of the boundary alter the observability of the first end surface 52. First end surface 52 may have a mark, or band of color applied to it which is normally visible to an observer because the refraction boundary acts to reflect light outward (i.e. toward an observer), making the image at first end surface 52 visible as a line. When pad 80 becomes saturated up to the area where pad 80 is in contact with second surface 54, the refractive boundary changes to transmit more light (or refract less light) so the image at first end surface 52 is no longer visible to the observer. First end surface 52 could also simply be transparent, such that the image or "mark" is actually the mating surface 32 of handle second end 24. The annulus 54 of wrap-around light pipe 50 receives a portion of pad 80 through it, snuggly fitting around pad 80 to assist holding and stabilizing pad 80 and to ensure adequate contact between pad 80 and the sufficiency indicator surface.

Sealing member 60 couples to sufficiency indicator end flanges 56 and 57 to seal against the interior surface 106 of pad compression tube 100. The exterior circumference of sealing member 60 is adapted to match the cross section of pad compression tube interior surface 106 in order seal against it. Sealing member 60 is annular to receive pad 80 therethrough, and includes a first lip 62 which engages pad 80, to hold it tighter and enhance the sealing effect, and a second lip 64 which couples to sufficiency indicator 50, which in the embodiment acts as an extension of handle 20 to provide a water tight seal around the retained end 82 of pad 80. The positions of sealing member 60 and sufficiency indicator 50 could be reversed as well. In the embodiment, sealing member 60 includes sealing flanges at either end to seal against pad compression tube interior surface 106. A single sealing surface could also function for the purpose. The double-ended seals provide an advantage of improved sealing and better maintaining alignment during compression.

In the first embodiment, sample collection pad 80 includes a full cross section portion 86 extending from the free end 84 of the sample collection pad 80 to a shoulder 90 formed at a location between the opposing ends 82 and 84 of the sample collection pad 80, and a reduced cross section portion 88 contained at least partially within the handle second end 24. Seal member first lip 62 engages the sample collection pad 80 at shoulder 90. Additionally, an angled surface 92 is formed into pad 80 having approximately the same angle of incidence as light pipe second surface 54 to conform with the light pipe second surface 54, thereby enhancing contact at the refractive boundary for more reliable indication. Therefore, in the embodiment, reduced cross section portion 88 actually includes two reduced cross section portions 94 and 96. The narrower portion 94 fits snuggly into the cavity 34 formed into handle second end 24, defined by end wall 38 and side wall 36 extending therefrom. A second side wall 40 extends to end surface 42 to receive sufficiency indicator extension flange 56 therein and abut tightly against sufficiency indicator 50. Sufficiency indicator 50 and handle second end 24 thereby form a substantially watertight cavity 34/70 to retain pad 80 retained end 82.

Referring to FIGS. 4, 5 and 10-12, in the first embodiment sufficiency indicator 50 includes a plurality of channels 58 extending lengthwise along at least the portion of the sufficiency indicator interior annulus 60 in contact with the sample collection pad 80. In the embodiment, sufficiency indicator 50 includes extension flanges 56 and 57 which provide coupling with handle second end 54 and sealing member 70, respectively. Channels 58 extend the entire length of sufficiency indicator 50, from end to end, and align with corresponding channels 68 through sealing member 70, which extend along the length of sealing member 70 interior surface. Channels 58 and 68 provide a vent path for displaced air to escape from pad 80 during sample collection as liquid wicks toward the sample collection pad retained end 92 and sufficiency indicator 50, thereby improving linear flow rates, as indicated by the flow arrows in FIG. 10. In the embodiment wrap-around light pipe 50 includes three ventilation channels 58 disposed symmetrically around the inner surface of light pipe 250. Each of ventilation channels 58 extend the length of light pipe 50, extending under sealing member 60 to the exposed full cross section portion 86 of specimen collection pad 80.

Referring to FIG. 1, a first embodiment includes a fluid sample filter 122 in-line with one or more pad compression tube outlets 108 or 118 and 120, the filter 122 in fluid communication with the respective in-line outlet ports 108 or 118 and 120 and the pad compression tube interior 106 or 116, respectively, to filter a liquid sample expressed through each of the respective in-line outlet ports. A single filter 122 may be disposed in a pad compression tube 100 to filter all outlet ports, or may be disposed within an outlet port, or externally to an outlet port, so as to be in-line with a single outlet port, say 118 while leaving remaining outlet ports 120 unfiltered. Alternatively, one or more filters 122 may be placed in-line external to one or more outlet ports 108, 118, 120, between the ports and one or more collection tubes 140.

In the embodiment, pad compression tubes 100 and 110 include collars 124 and 126, respectively, disposed proximal to the pad compression tube first open ends 102 and 112. The collars 124, 126, provide a point to hold the pad compression tubes during compression and provide stiffening for the open ends.

Figure 15:
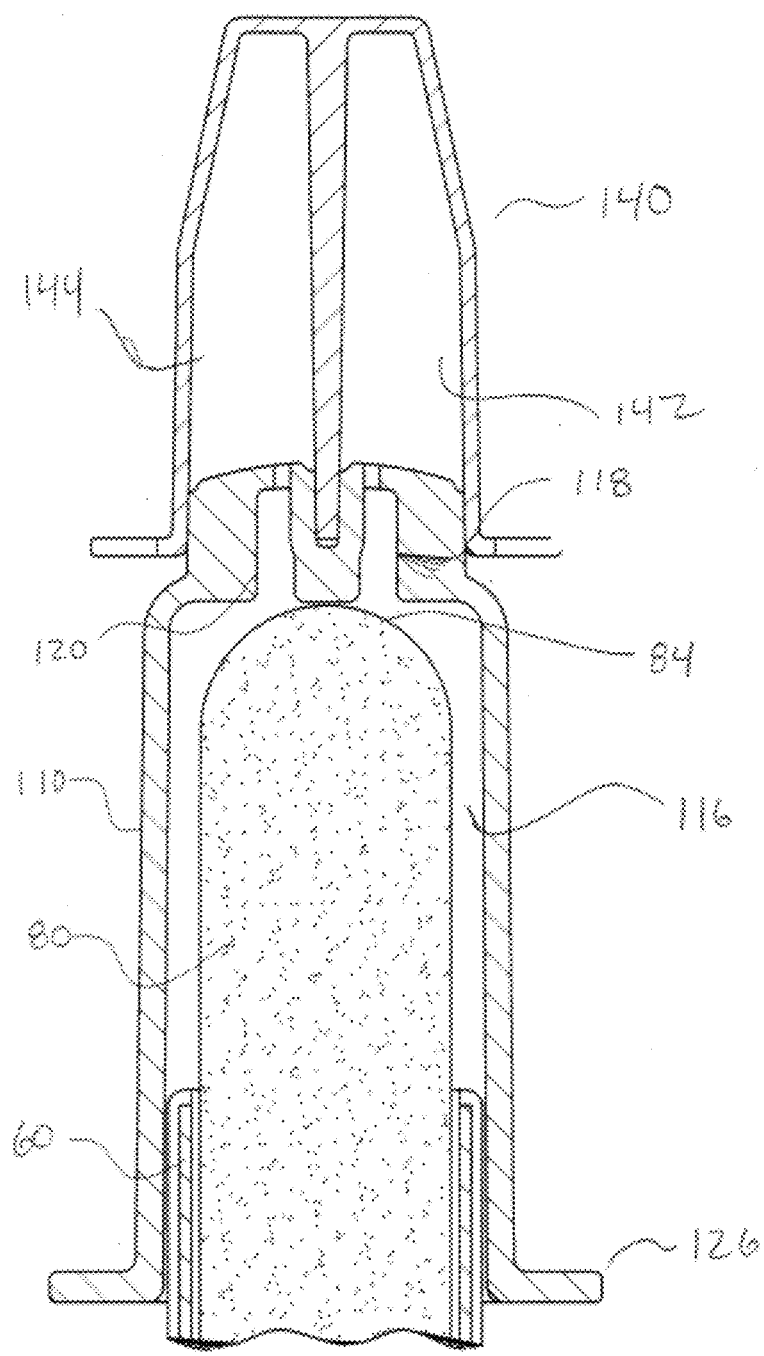
FIG. 15 shows a cutaway view of a first embodiment with a collection tube.

Referring to FIG. 15, an embodiment is shown with a collection tube 140 having a plurality of collection chambers 142 and 144 attachable to the one or more pad compression tube outlet ports, each collection tube having one or more sample chambers, wherein when a collection tube is attached to a pad compression tube outlet port, the respective one or more sample chambers are in fluid communication with the pad compression tube interior.

In the embodiment, the handle 20 is made from polypropylene, polycarbonate, polyethylene, polytetrafluoroethylene, enamel, nylon, ceramic, or a combination thereof, to provide compatibility with chemical process and permit sterilization, while maintaining reasonably low costs for mass production. Overall, the shape of the handle 20 as defined at least in part by the handle grip member 28 may provide the specimen sample collection system 10 with substantial grip and control. Further, as the handle grip member 28 is approximately skeletal in nature, the handle 20 may exhibit substantial rigidity and effective handle 20 thickness (e.g., as grasped by a sample collecting technician or fluid sample provider) without requiring a substantial volume of constituent material, for example if the handle 20 is molded from, at least in part, polypropylene, polycarbonate, polyethylene, polytetrafluoroethylene (PTFE), enamel, nylon, and/or a combination thereof. In an embodiment, the handle 20 may include one or more shapes and/or features to increase the ergonomics of the handle 20 and/or ease and stability with which the handle 20 (including the sample collection pad 80 coupled thereto) may be deployed to collect a fluid sample. For example, in an embodiment, the handle 20 may include a handle grip member 28. The handle grip member 28 may increase the security with which the handle 20 may be grasped. More specifically, the handle grip member 28 may include a plurality of ribs and/or ridges to increase the grip of the handle 20. In an embodiment, the handle 20 may include the handle grip member 28 on a portion of the circumference of the handle 20, for example adjacent the fingers if the handle 20 were grasped in a hand. Alternately, the handle grip member 28 may at least in part extend substantially around the circumference of the handle 20. Further, the handle grip member 28 may extend either partially or substantially completely along the length of the handle 20 (e.g., along its longitudinal axis).

In the embodiment, sample collection pad 80 is made from polyolefin, nylon, cellulose, or any other absorbent material, or combination thereof. For example, the material of the sample collection pad 80 may be determined at least in part by its compatibility with and/or affinity for the fluid sample to be collected. More specifically, the sample collection pad 80 may be formed at least in part from polyolefin, nylon, cellulose, or any other absorbent material, or combination thereof. In an embodiment, the sample collection pad 80 material may at least in part adsorb a fluid sample and may create an adsorbate at the surface of the sample collection pad 80 from which a fluid sample may be collected. Alternatively or additionally, the sample collection pad 80 may be formed at least in part of an absorbent material into which the sample fluid may diffuse and from which a sample may be collected. In the embodiment, a test strip is disposed within the handle and observable by a user to provide contemporaneous test results, the test strip in fluid communication with the sample collection pad.

In addition to material, the size and/or volume of the sample collection pad 80 may be configured to collect a variety of fluid samples from a variety of fluid sources. In combination with the material of the sample collection pad 80, the size and/or volume of the sample collection pad 80 may determine the volume of fluid that may be collected by a specific sample collection pad 80 configuration. For example, a sample collection pad 80 may be configured to collect saliva from an adult human mouth. For such an embodiment, the sample collection pad 80 may collect at least 0.5 milliliter of saliva. Alternately, a relatively smaller sample collection pad 80 may be configured to collect saliva from an infant human mouth. For such an embodiment, the relatively smaller sample collection pad 80 may collect at least 0.2 milliliter of saliva. Alternately still, a relatively larger sample collection pad 80 may be configured to collect saliva from a large animal (e.g., cow, horse, and/or any other domesticated, captive, captive-bred, or wild animals). The embodiments are not limited in this context.

In an embodiment for which sample collection pad 80 is configured to collect a saliva sample from a human or animal, the specimen sample collection system 10 may include an additive to encourage the production of saliva when the sample collection pad 80 is inserted into the mouth of the human or animal from which the sample is to be collected. For example, in an embodiment, the sample collection pad 80 may include one or more additives such as salt, citric acid, or any other saliva-encouraging additive or a combination thereof to encourage and/or promote saliva production. Alternately, the additive may be provided separate from the sample collection pad 80. In an embodiment, the additive may increase the ease with which an adequate saliva sample may be generated and collected by the sample collection pad 80, for example by reducing the duration of time that the sample collection pad 80 may remain in the mouth of the human or animal.

Further, the material and size of the sample collection pad 80 may at least in part determine the amount of fluid to be collected before the sample volume adequacy indicator 50 indicates that an adequate volume of fluid has been collected. Said differently, for any type of fluid for which the specimen sample collection system 10 is configured to collect, the sample volume adequacy indicator 50 may indicate if and when a predetermined volume of sample fluid has been collected (i.e., absorbed) by the sample collection pad 80. The predetermined volume of sample fluid may be configured at least in part to satisfy one or more fluid sample testing procedures and/or protocols.

The handle 20 may further include one or more handle thumb detents 24 adjacent the thumb if the handle 20 were grasped in a hand. In an embodiment, the thumb detent 24 may alternately extend substantially completely around the circumference of the handle 20. For either embodiment, the handle thumb detent 24 may be formed a substantially narrow portion of the handle 20 including a substantially arcuate cross section to better engage a grasping thumb.

The handle 20 of an embodiment functions to not only help collect a fluid sample with the sample collection pad 80, but to also aid the discharge and/or release of the fluid sample from the sample collection pad 80. As such, the handle 20 may further include a thumb pad 26 that, in cooperation with the pad compression tube collar 124, may allow the sample collector to squeeze the handle 20 and pad compression tube 60 together to compress the sample collection pad 80 within pad compression tube 100 once inserted therein. The compression of the sample collection pad 80 within the pad compression tube 100 may thereby discharge the collected fluid sample.

Referring to FIG. 15, an embodiment with a collection tube 140 is shown, having a plurality of sample chambers 142 and 144. Collection 140 may include preservative buffer solutions as well. The buffer solution may incorporate various components available as off the shelf reagents. Minimally the buffer solution may contain a lysis reagent to lyse the cells and a preservative agent to stabilize the components in the collected fluid sample for a period of several months. Guanidine is one agent known to preserve genetic samples (e.g., DNA and/or RNA) for long periods of time. Other buffer solutions may be provided in or with the buffer container consistent with an embodiment of specimen sample collection system 10. The type and volume of the buffer solution may depend in part based on the volume and type of the collected sample fluid, for example as determined by the sample collection pad 80.

Figure 16:
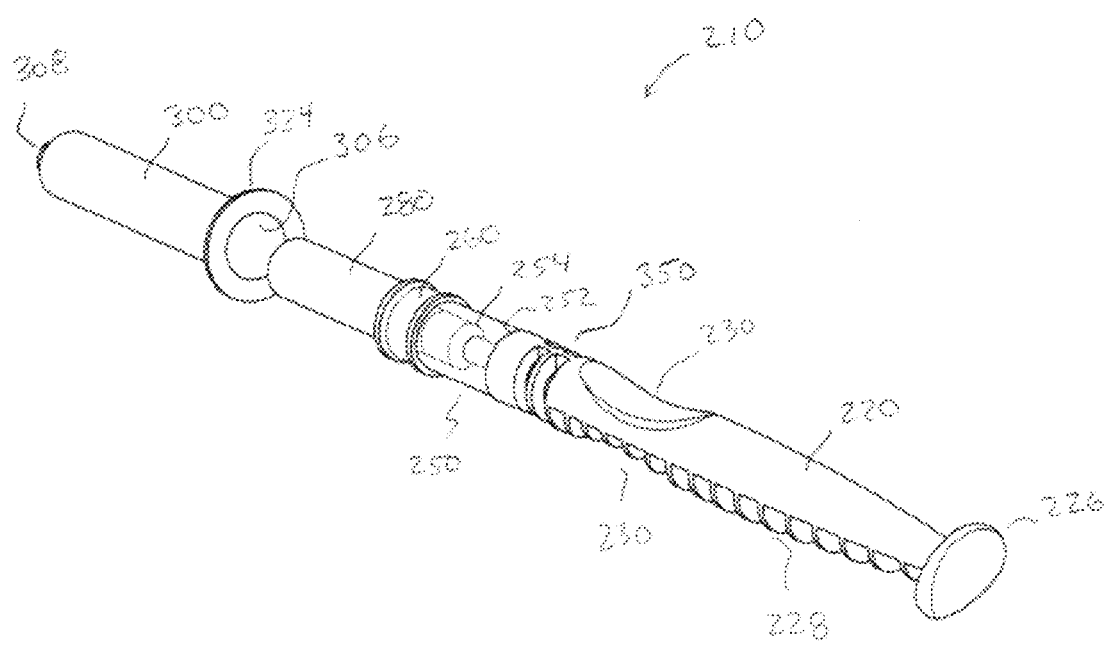
FIG. 16 shows a perspective view of a second embodiment.

Referring to FIG. 16, a second embodiment of a specimen sample collection device system 200 is shown, which is very similar to the first embodiment, including a sample collection device 210, pad compression tube 300, and collection tube (not shown) for attaching to the outlet 308 of pad compression tube 300. Sample collection device 210 includes round cylindrical specimen collection pad 280, made from absorbent material, which inserts into collector handle 220, sealing member 270, and sample volume adequacy indicator 250. Collector handle 220 preferably includes gripping member 228, thumb pad 226 and finger detents 230 for firm ergonomic gripping. Handle 220 includes an additional vented wrap-around gripping portion 350 for improved ergonomics.

The round cylindrical shape of specimen collection pad 280 provides efficient volume for collection of liquid saliva sample, and provides more uniform compression characteristics than traditional flat specimen collection pads. Specimen collection pad 280 includes a narrow extension which extends into handle 220 for attachment, as well as providing a wicking channel which maintains contact with adequacy indicator 250.

Sealing member 270 includes a first and second flange seals 330 and 332 for sealing against the inner wall of pad compression tube 300 as specimen collection pad 280 is compressed to express liquid sample. Preferably second flange seal 332 is provided, spaced apart from first flange seal 330 along the axial length of collector handle 220. Second flange seal 332 provides a secondary seal as well as aiding in maintaining alignment of sample collector 210 as it is inserted into pad compression tube 300. Preferably pad compression tube 300 includes a pad seat with buffer material such that buffer material is mixed with liquid sample as the liquid sample is expressed through pad compression tube outlet 308.

Sample adequacy indicator 250 is preferably a wrap-around light pipe. As shown in FIG. 16, light pipe 250 includes a first surface 252 which is aligned normal to the long axis of collector handle 220, and a second surface 254 at an angle of incidence to 252 First surface 252 is provided with a color coating or a pattern, and second surface 254 provides visual indication to the user of saturation by alteration of the refraction characteristics. Specimen collection pad 280 is in physical contact with second surface 254. With specimen collection pad 280 dry, or at least not saturated all the way to the region of light pipe 250, light reflected from first surface 252 is refracted radially outward when encountering second surface 254, so that a user sees a colored or patterned band at second surface 254. When specimen collection pad 280 becomes saturated with liquid sample to the region of light pipe 250, the refractive characteristics of the boundary between second surface 254 and specimen collection pad 280 (now saturated with liquid) alter so that less light is refracted at the boundary and more light is transmitted through the boundary, such that the colored or patterned band is no longer visible.

Other sample volume adequacy indicators could also be compatible with this embodiment, as described above. Wrap-around light pipe 250 has several additional advantages. The light pipe avoids potential contamination of liquid samples in devices using dilution or migration of dyes for adequacy indication. The light pipe is easily manufactured from plastic and easily assembled with the device. The light pipe and the wrap-around light pipe are easily sealed so as to provide efficient compression and expression of liquid sample using pad compression tube 300. The wrap-around light pipe allows the medical technician to observe the sampling in real time, so there is no need to remove the sample collector from the patient's mouth to check the adequacy indicator, thereby avoiding potential contamination problems. The light pipe provides a clear go/no-go indicator of sample adequacy, whereas devices using dilution or migration of dyes require some interpretation and guess work by the user.

The embodiments of the present invention are compatible with a variety of specimen collection pad materials, which can be interchanged depending on the targeted analytes, proteins or chemicals. The use of non-detaching specimen collection pads in combination with pad compression tubes provides for simplified and more reliable testing procedures. The specimen collection pad itself is more securely held in the sample collection device. There is no danger of dropping the specimen collection pad while trying to detach the pad and insert it into a buffer solution, which would contaminate the sample and which poses a contagion hazard. There is no requirement to centrifuge the specimen collection pad to remove liquid sample. The specimen collection pad compressed and locked into the pad compression tube can still be preserved for future verification testing, and the pad compression tube or handle are more easily labeled with sample identifier information. The sample collection system as described herein is substantially "idiot-proof", preventing inadvertent mistakes by poorly trained field personnel (who might not have any medical training at all) working in harsh climates and unsanitary environments, which could render samples unusable or spread disease.

Use of the first embodiment is described. A specimen sample collection system is easily manufactured and assembled by mass production methods because the component parts slip fit together in a linear fashion. Sufficiency indicator 50 flange 56 slips into handle cavity 34 to couple with end wall 38 and side wall 36, forming a substantially watertight cavity to receive pad 80. Sealing member 60 is inserted over flange 57, ensuring sufficiency indicator internal channels 58 align with sealing member internal channels 68. Specimen collection pad 80 is inserted with its retained end 82 fitting snuggly into cavity 34, and angled surface 92 abutting against light pipe second surface 54, and shoulder 90 abutting and engaging with sealing member lip 62. The collector is inserted into a subject's mouth or a fluid sample, pad free end 82 first, to absorb and wick fluid into pad 80. As pad 80 wicks fluid during sample collection air is pushed out of the pad 80 through interior channels 58 and 68 to provide faster and more complete saturation of pad 80. When pad 80 is saturated sufficiently, after approximately 1-2 minutes, the line visible at refraction boundary 54/92 will disappear, and the device may be withdrawn. A pad compression tube, such as 110 may then be inserted over the pad 80 and the handle second end 24, and a collection tube (such as 140) connected to outlet ports 118 and 120 to receive liquid sample expressed as pad compression tube 110 is compressed onto pad 80.

Sealing member 60 seals against the interior surface 116 of pad compression tube 110, and the friction causes first lip 62 to grip pad 80 tighter, and compresses sufficiency indicator 50 more tightly against handle second end 24 to provide a tighter seal, preventing liquid from leaking out through the indicator/handle junction. Sealing member 60 transfers linear force to pad 80 by engaging shoulder 90 with lip 62, thereby providing more thorough and even compression of pad 80. Handle grip members 28 and detents 30 provide ergonomic gripping areas for comfort and accurate manipulation when inserting into a mouth or pad compression tube. Pad compression tube flange 126 and thumb pad 26 provide leverage points to squeeze pad 80 with only one hand.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

We claim:

1. A specimen sample collection system comprising:
a handle having opposing first and second ends, and a sufficiency indicator coupled to the handle, wherein the handle second end and sufficiency indicator form a cavity adapted to receive a sample collection pad;
a sample collection pad having opposing ends, the sample collection pad partially contained within and extending from the handle second end and in contact with the sufficiency indicator, the sample collection pad having a cylindrical cross section;
a pad compression tube having a first open end to go over the sample collection pad and second end of the handle, an opposing second end, an interior surface extending therebetween, and at least outlet port proximal to the pad compression tube second end and in fluid communication with the pad compression tube interior; and,
wherein the sufficiency indicator comprises a light pipe, the light pipe including a first end surface and a second surface in physical contact with the sample collection pad creating a refractive boundary, the second surface oriented at an angle of incidence to the first end surface such that when the sample collection pad absorbs a sufficient liquid sample the refractive properties of the boundary alter the observability of the first end surface.

2. The system of claim 1, further comprising:
wherein the handle further includes grip members disposed along at least a portion of the handle proximal to the first end.

3. The system of claim 1, further comprising:
the handle first end further including a thumb pad.

4. The system of claim 1, further comprising:
wherein the sample collection pad cylindrical cross section is substantially round.

5. The system of claim 1, further comprising:
wherein the sample collection pad cylindrical cross section is substantially square.

6. The system of claim 1, further comprising:
wherein the sufficiency indicator comprises an annular portion coupled to handle second end to form an extension of the handle.

7. The sys of claim 1, the further comprising:
an annular seal member coupled to the handle and having outer perimeter sized to form a watertight barrier against a pad compression tube interior surface.

8. The system of claim 7, the seal member further comprising a lip to engage the sample collection pad.

9. The system of claim 1, the sample collection pad further comprising:
a full cross section portion extending from the free end of the sample collection pad to a shoulder formed at a location between the opposing ends of the sample collection pad; and,
a reduced cross section portion contained at least partially within the handle second end.

10. The system of claim 9, further comprising:
a seal member coupled to the handle proximal to the handle second end, the seal adapted to form a watertight barrier against a pad compression tube interior surface and having a lip to engage the sample collection pad at the shoulder.

11. The system of claim 1, further comprising:
a fluid sample filter in-line with one or more pad compression tube outlets, the filter in fluid communication with the respective in-line outlet ports and the pad compression tube interior to filter a liquid sample expressed through each of the respective in-line outlet ports.

12. The system of claim 1, wherein the pad compression tube includes a plurality of outlet ports, and further comprising:
two or more fluid sample filters, each of the two or more filters in-line with a single outlet port and in fluid communication with its respective outlet port and the pad compression tube interior to filter a liquid sample expressed through the respective in-line outlet port.

13. The system of claim 1, the pad compression tube further comprising:
a pad compression tube collar disposed proximal to the pad compression tube first open end.

14. The system of claim 1, further comprising:
one or more collection tubes attachable to the one or more pad compression tube outlet ports, each collection tube having one or more sample chambers, wherein when a collection tube is attached to a pad compression tube outlet port, the respective one or more sample chambers are in fluid communication with the pad compression tube interior.

15. The system of claim 1, the handle further comprising polypropylene, polycarbonate, polyethylene, polytetrafluoroethylene, enamel, nylon, ceramic, or a combination thereof.

16. The system of claim 1, the sample collection pad further comprising polyolefin, nylon, cellulose, or any other absorbent material, or combination thereof.

17. The system of claim 1, further comprising a test strip disposed within the handle and observable by a user to provide contemporaneous test results, the test strip in fluid communication with the sample collection pad.

18. A specimen sample collection system comprising:
a handle having opposing first and second ends, and a sufficiency indicator coupled to the handle, wherein the handle second end and sufficiency indicator form a cavity adapted to receive a sample collection pad;
a sample collection pad having opposing ends, the sample collection pad partially contained within and extending from the handle second end and in contact with the sufficiency indicator, the sample collection pad having a cylindrical cross section; and,
a pad compression tube having a first open end to go over the sample collection pad and second end of the handle, an opposing second end, an interior surface extending therebetween, and at least outlet port proximal to the pad compression tube second end and in fluid communication with the pad compression tube interior;
wherein the sufficiency indicator is an wrap-around light pipe of substantially annular shape and a portion of the sample collection pad extends into the annulus of the wrap-around light pipe, the light pipe including a first end surface and a second surface in physical contact with the sample collection pad creating a refractive boundary, the second surface oriented at an angle of incidence to the first surface such that when the sample collection pad absorbs a sufficient liquid sample the refractive properties of the boundary alter the observability of the first end surface.

19. The system of claim 18, the sample collection pad further comprising an angled surface formed into the pad to conform with the light pipe second surface.

20. The system of claim 6, further comprising:
wherein the sufficiency indicator includes a plurality of grooves extending lengthwise along at least the portion of the sufficiency indicator interior in contact with the sample collection pad.

21. The system of claim 18, further comprising:
wherein the wrap-around light pipe includes a plurality of grooves extending lengthwise along at least the portion of the sufficiency indicator interior in contact with the sample collection pad.

22. A specimen sample collection system, comprising:
a handle including a sufficiency indicator and means for providing a water tight seal between said handle and a pad compression tube insertable over said handle;
an sample collection pad partially contained within said handle, said sample collection pad comprising round cylindrical shape;
a pad compression tube insertable over said sample collection pad within said handle and around an end of said handle, said pad compression tube including one or more outlet ports; and,
one or more collection tubes having one or more sample chambers, attachable to said one or more pad compression tube outlet ports, and wherein said compression tube defines one or more chambers in fluid communication with said one or more pad compression tube outlet ports, and wherein when said collection tube is attached to said one or more pad compression tube outlet ports, the chambers are in fluid communication with said pad compression tube;
wherein said sufficiency indicator is a wrap-around light pipe of substantially annular shape and a portion of said sample collection pad extends into the annulus of said wrap-around light pipe, said light pipe including a first end surface with a marking and a second surface in physical contact with said sample collection pad creating a refractive boundary, said second surface oriented at an angle of incidence to said first surface such that when the sample collection pad absorbs a sufficient liquid sample the refractive properties of said boundary alter the observability of the mark.

23. The system of claim 22, wherein said means for providing a watertight seal comprises a plunger, said plunger being substantially annular and disposed over an end of said handle for receiving said sample collection pad through the center of said plunger.

24. The system of claim 23, wherein said plunger includes first and second flange seals at distal ends of said plunger for sealing against the interior of said pad compression tube.

25. The system of claim 22 wherein said wrap-around light pipe extends through the interior annulus of said sealing means, and wherein said wrap-around light pipe includes a plurality of interior axial grooves extending substantially the length of said wrap-around light pipe, said grooves in fluid communication with a portion of said sample collection pad not contained within said handle and with a portion of said sample collection pad extending into the annulus of said wrap-around light pipe.

26. The system of claim 22 further comprising a pad seat, said pad seat disposed within said pad compression tube proximally to said pad compression tube outlet ports, wherein said pad seat contains buffer material.

27. The system of claim 26, wherein said pad seat buffer material comprises a wetted solution.

28. The system of claim 26, wherein said pad seat buffer material comprises a lyophilized buffer material applied to said pad seat in a dry condition.

29. The system of claim 26, wherein said pad seat buffer material comprises a lyophilized buffer material applied to said pad seat in a wet condition, and wherein said pad seat including said wet buffer solution is lyophilized.

30. A specimen sample collection system, comprising:
a handle including a sufficiency indicator and a plunger;
an sample collection pad partially contained within said handle to absorb a fluid sample, the sample collection pad having a round cylindrical shape;
a pad compression tube including one or more outlet ports, the pad compression tube to receive at least the sample collection pad and the plunger, the plunger to provide a water tight seal between the handle and the pad compression tube;
wherein said sufficiency indicator is a wrap-around light pipe of substantially annular shape and a portion of said sample collection pad extends into the annulus of said wrap-around light pipe to indicate a sufficiency of the fluid sample.

31. The system of claim 30, the wrap-around light pipe further comprising a first end surface having a marking and a second surface in physical contact with the sample collection pad to create a refractive boundary, the second surface oriented at an angle of incidence to the first surface such that when the sample collection pad absorbs the sufficient fluid sample the refractive properties of the refractive boundary alter the observability of the mark to indicate collection of the sufficient fluid sample.

32. The system of claim 30 further comprising one or more collection tubes each having one or more sample chambers, the one or more collection tubes to couple to the one or more pad compression tube outlet ports, the one or more collection tubes to receive the fluid sample from the sample collection pad when the sample collection pad is compressed in the pad compression tube.

33. The system of claim 30, the plunger further comprising a first flange seal and a second flange seal at distal ends of the plunger to seal against the interior of the pad compression tube when the sample collection pad and the plunger are inserted into the pad compression tube.

34. The system of claim 30, the wrap-around light pipe further comprising a plurality of interior axial grooves extending substantially the length of the wrap-around light pipe, the axial grooves in fluid communication with at least a portion of the sample collection pad not contained within said handle and with a portion of the sample collection pad extending into the annulus of the wrap-around light pipe.

35. The system of claim 30 further comprising a pad seat, the pad seat disposed within the pad compression tube proximate to the one or more pad compression tube outlet ports, the pad seat further including a buffer material.

36. The system of claim 35, the pad seat buffer material further comprising a wetted solution.

37. The system of claim 35, the pad seat buffer material further comprising a lyophilized buffer material applied to the pad seat in a dry condition.

38. The system of claim 35, the pad seat buffer material further comprising a lyophilized buffer material applied to the pad seat in a wet condition, wherein the pad seat including the wet buffer solution is lyophilized.

* * * * *